United States Patent
Dinsmore et al.

(10) Patent No.: US 6,432,711 B1
(45) Date of Patent: Aug. 13, 2002

(54) EMBRYONIC STEM CELLS CAPABLE OF DIFFERENTIATING INTO DESIRED CELL LINES

(75) Inventors: Jonathan H. Dinsmore, Brookline; Judson Ratliff, Stoneham, both of MA (US)

(73) Assignee: Diacrin, Inc., Charlestown, MA (US)

( * ) Notice: Subject to any disclaimer, the term of this patent is extended or adjusted under 35 U.S.C. 154(b) by 0 days.

(21) Appl. No.: 08/333,076

(22) Filed: Nov. 1, 1994

Related U.S. Application Data

(63) Continuation-in-part of application No. 08/145,175, filed on Nov. 3, 1993, now abandoned.

(51) Int. Cl.$^7$ ............................. C12N 5/08; C12N 5/00; C12N 5/02
(52) U.S. Cl. ...................... 435/368; 435/325; 435/366; 435/384; 435/386
(58) Field of Search .................. 435/240.2, 240.21, 435/240.3, 325, 366, 368, 384, 386

(56) References Cited

U.S. PATENT DOCUMENTS

| | | | | |
|---|---|---|---|---|
| 4,626,507 A | * | 12/1986 | Trowbridge et al. ......... | 435/240 |
| 5,087,570 A | * | 2/1992 | Weissman et al. ......... | 435/240.1 |
| 5,128,245 A | * | 7/1992 | Greenberg et al. ............. | 435/29 |
| 5,166,065 A | * | 11/1992 | Williams et al. .......... | 435/240.1 |
| 5,340,740 A | * | 8/1994 | Petitte et al. ............. | 435/240.2 |
| 5,366,888 A | * | 11/1994 | Fry et al. ................ | 435/240.21 |
| 5,475,006 A | * | 12/1995 | Burton et al. ................ | 514/310 |

FOREIGN PATENT DOCUMENTS

| | | |
|---|---|---|
| DE | 299429 | 4/1992 |
| WO | WO90/03432 | 4/1990 |

OTHER PUBLICATIONS

Spooncer et al. Differentiation. vol. 31 (2), pp. 111–118, 1986.*
Lathrop et al. J. Cell Biol. vol. 100(5), pp. 1540–1547, 1985.*
Yamamori, T. et al., Science, vol. 246, p. 1412–16, Dec. 1989.*
Fukuchi, K. et al., Neuroscience Letters, vol. 154 (1–2), p. 145–48, 1993.*
Bain, G. et al., Molecular Brain Research, vol. 17(1–2), p. 23–30, 1993.*
Tajbakhsh, S. et al., Neuron, vol. 13(4), p. 813–21, 1994.*
Rose, O. et al., Developmental Dynamics, vol. 201(3), pp. 245–259, 1994.*
Wobus, A.M. et al., Roux's Arch. Dev. Biol., vol. 204(1), pp. 36–45, 1994.*
Wheeler, M.B., Reprod. Fertil. Dev., vol. 6(5), pp. 563–568, 1994.*
Martin, et al., *Proc. Nat. Acad. Sci.,* vol. 72, No. 4, pp. 1441–1445 (Apr. 1975).
Doetschman, et al., *J. Embryol. Exp. Morph.,* vol. 87, pp. 27–45 (1985).
Davis, et al., *Cell,* vol. 51, pp. 987–1000 (Dec. 24, 1987).
Wobus, et al., *Biomed. Biochem. Acta,* vol. 47, pp. 965–973 (1988).
Doetschman, et al. *Developmental Biology,* vol. 127, pp. 224–227 (1988).
Fisher, et al., *Experimental Cell Research,* vol. 182, pp. 403–414 (1989).
Pease, et al., *Developmental Biology,* vol. 141, pp. 344–352 (1990).
Evans, et al., *Theriogenology,* vol. 33, No. 1, pp. 125–128 (Jan. 1990).
Robbins, *J. Biol. Chem.,* vol. 265, No. 20, pp. 11905–11909 (Jul. 15, 1990).
Piedrahita, et al., *Theriogenology,* vol. 34, No. 5, pp. 865–877 (Nov. 1990).
Wiles, et al., *Development,* vol. 111, pp. 259–267 (1991).
Schmitt, et al., *Gene & Development,* vol. 5, pp. 728–740 (1991).
Gutierrez–Ramos, et al., *Proc. Nat. Acad. Sci.,* vol. 89, pp. 9171–9175 (Oct. 1992).

* cited by examiner

Primary Examiner—Christopher R. Tate
(74) Attorney, Agent, or Firm—Elliot M. Olstein

(57) ABSTRACT

An embryonic stem cell which may be induced to differentiate homogeneously into a desired primary cell line. The embryonic stem cell may be engineered with DNA, which encodes a protein or polypeptide which promotes differentiation of the stem cell into a specific cell line, such as, for example, a neuronal cell line, a muscle cell line, or a hematopoietic cell line. The DNA may encode a transcription factor found in the particular cell line. In another alternative, a desired cell line is produced from embryonic stem cells by culturing embryonic stem cells under conditions which provide for a three-dimensional network of embryonic stem cells, and then stimulating embryonic stem cells with an agent, such as retinoic acid, or dimethylsulfoxide, which promotes differentiation of the embryonic stem cells into the desired cell line, such as, for example, a neuronal cell line, or a muscle cell line.

7 Claims, No Drawings

EMBRYONIC STEM CELLS CAPABLE OF DIFFERENTIATING INTO DESIRED CELL LINES

This application is a continuation-in-part of application Ser. No. 08/145,175, filed Nov. 3, 1993 now abandoned.

This invention relates to embryonic stem cells. More particularly, this invention relates to embryonic stem cells which are engineered with DNA and/or cultured in the presence of an agent, whereby such cells become capable of differentiating homogeneously into a desired primary cell line. Such homogeneous differentiation has not and cannot be achieved unless the methods described herein are applied.

Embryonic stem cells are pluripotent cells derived from the inner cell mass of pre-implantation embryos. (Evans et al., *Nature*, Vol. 292, pgs. 154–156 (1981)). Embryonic stem cells can differentiate into any cell type in vivo (Bradley, et al., *Nature*, Vol. 309, pgs. 255–256 (1984); Nagy, et al., *Development*, Vol. 110, pgs. 815–821 (1990) and into a more limited variety of cells in vitro (Doetschman, et al., *J. Embryol. Exp. Morph.*, Vol. 87, pgs. 27–45 (1985); Wobus, et al., *Biomed. Biochim. Acta*, Vol. 47, pgs. 965–973 (1988); Robbins, et al., *J. Biol. Chem.*, Vol. 265, pgs. 11905–11909 (1990); Schmitt, et al., *Genes and Development*, Vol. 5, pgs. 728–740 (1991)). Embryonic stem cells, however, are more difficult to maintain in the laboratory and require the addition of a differentiation inhibitory factor (commonly referred to as leukemia inhibitory factor (or LIF) in the culture medium to prevent spontaneous differentiation (Williams, et al., *Nature*, Vol. 336, pgs. 684–687 (1988); Smith, et al., *Nature*, Vol. 336, pgs. 688–690 (1988); Gearing, et al,, *Biotechnology*, Vol. 7, pgs. 1157–1161 (1989); Pease, et al., *Dev. Biol.*, Vol. 141, pgs. 344–352 (1990). LIF is a secreted protein and can be provided by maintaining embryonic stem cells on a feeder layer of cells that produce LIF (Evans, et al., 1981; Robertson, *Teratocarcinomas and Embryonic Stem Cells: A Practical Approach*, Washington, D.C.: IRL Press (1987)) or by the addition of purified LIF (Williams, et al., 1988; Smith, et al., 1988; Gearing, et al., 1989; Pease, et al., *Exp. Cell Res.*, Vol. 190, pgs. 209–211 (1990) to the medium in the absence of feeder layers. Differentiation of embryonic stem cells into a heterogeneous mixture of cells occurs spontaneously if LIF is removed, and can be induced further by manipulation of culture conditions (Doetschmann, et al., 1985; Wobus, et al., 1988; Robbins, et al., 1990; Schmitt, et al., 1991; Wiles, et al., *Development*, Vol. 111, pgs. 254–267 (1991); Gutierrez-Ramos, et al., *Proc. Nat. Acad. Sci.*, Vol. 89, pgs. 9111–9175 (1992)). Differentiation of stem cells into a homogeneous population, however, has not been achieved. Embryonic stem cell differentiation can be variable between different established embryonic stem cell lines and even between laboratories using the same embryonic stem cell lines.

It is an object of the present invention to provide embryonic stem cells which are capable of differentiating uniformly into a specific and homogeneous cell line, not achievable by previous methods.

In accordance with an aspect of the present invention, there is provided a method of producing a desired cell line from embryonic stem cells. The method comprises culturing embryonic stem cells under conditions which promote growth of the embryonic stem cells at an optimal growth rate. The embryonic stem cells then are cultured under conditions which promote the growth of the cells at a rate which is less than that of the optimal growth rate, and in the presence of an agent which promotes differentiation of the embryonic stem cells into the desired cell line.

In general, a growth rate which is less than the optimal growth rate, is a growth rate from about 10% to about 80%, preferably from about 20% to about 50%, of the maximum growth rate for embryonic stem cells. The growth rates for embryonic stem cells can be determined from the doubling times of the embryonic stem cells. In general, the optimum doubling time for embryonic stem cells is from about 13 hours to about 18 hours, and more particularly, from about 15 hours to about 16 hours.

In one embodiment, when the embryonic cells are being cultured under conditions which promote growth of the cells at an optimal growth rate, the embryonic stem cells are cultured in the presence of a medium including leukemia inhibitory factor (LIF), and serum selected from the group consisting of: (i) horse serum at a concentration of from about 5% by volume to about 30% by volume; and (ii) fetal bovine serum at a concentration of from about 15% by volume to about 30% by volume. In one embodiment, the serum is horse serum at a concentration of about 10% by volume. In another embodiment, the serum is fetal bovine serum at a concentration of about 15% by volume.

In yet another embodiment, when the embryonic stem cells are cultured at an optimal growth rate, the embryonic stem cells are cultured in the absence of a feeder layer of cells.

In one embodiment, the agent which promotes differentiation of the embryonic stem cells is selected from the group consisting of retinoic acid and nerve growth factor, and the desired cell line is a neuronal cell line.

In one embodiment, in addition to culturing the cells in the presence of the stimulating agent selected from the group consisting of retinoic acid and nerve growth factor, the embryonic stem cells are grown in the presence of a cytokine. Cytokines which may be employed include, but are not limited to, Interleukin-1, Interleukin-3, Interleukin-4, Interleukin-6, colony stimulating factors such as M-CSF, GM-CSF, and CSF-1, steel factor, and erythropoietin.

In a further embodiment, the agent which promotes differentiation of the embryonic stem cells is selected from the group consisting of dimethylsulfoxide and hexamethylene bis-acrylamide, and the desired cell line is a muscle cell line, such as a smooth muscle cell line, or a skeletal muscle cell line, or a cardiac muscle cell line. In one embodiment, the agent is dimethylsulfoxide. In another embodiment, the agent is hexamethylene bis-acrylamide.

In one embodiment, in addition to culturing the embryonic stem cells in the presence of an agent which promotes differentiation of the embryonic stem cells into a muscle cell line, the embryonic stem cells also are grown in the presence of a cytokine, examples of which are hereinabove described.

In yet another embodiment, when the embryonic stem cells are cultured in the presence of the agent which promotes differentiation of the embryonic stem cells into a desired cell line, the embryonic stem cells also are cultured in the presence of fetal bovine serum at a concentration of about 10% by volume.

In a further embodiment, when the embryonic stem cells are cultured in the presence of the agent which promotes differentiation of the embryonic cells into a desired cell line, the embryonic stem cells also are cultured in a three-dimensional format.

Thus, Applicants have found that one may produce a homogenous desired cell line from embryonic stem cells by culturing the embryonic stem cells initially under conditions which favor the growth or proliferation of such embryonic stem cells at an optimal growth rate, and then culturing the cells under conditions which decrease the growth rate of the cells and promote differentiation of the cells to a desired cell type.

In a preferred embodiment, the embryonic stem cells cultured in a standard culture medium (such as, for example, Minimal Essential Medium), which may include supplements such as, for example, glutamine, and β-mercaptoethanol. The medium may also include leukemia inhibitory factor (LIF), or factors with LIF activity, such as, for example, CNTF or IL-6, and horse serum. LIF, and factors with LIF activity, prevents spontaneous differentiation of the embryonic stem cells, and is removed prior to the addition of the agent. Horse serum promotes differentiation of the embryonic stem cells into the specific cell type after the addition of the agent to the medium. After the cells have been cultured for a period of time sufficient to permit the cells to proliferate to a desired number, the cells are washed free of LIF, and then cultured under conditions which provide for the growth of the cells at a decreased growth rate but which also promote differentiation of the cells. The cells are cultured in the presence of an agent which promotes or stimulates differentiation of the embryonic stem cells into a desired cell line, and in the presence of fetal bovine serum at a concentration of from about 5% by volume to about 10% by volume, preferably at about 10% by volume. The presence of the fetal bovine serum at a concentration of from about 5% by volume to about 10% by volume, and of the agent, provides for growth or proliferation of the cells at a rate which is less than the optimal rate, while favoring the differentiation of the cells into a homogeneous desired cell type. The desired cell type is dependent upon the agent which promotes or stimulates the differentiation of the embryonic stem cells. The embryonic stem cells also are cultured in a three-dimensional format. Examples of such three-dimensional culturing formats are disclosed in Doetschman, et al., (1985), and in Rudnicki, et al., (1987).

For example, the embryonic stem cells may be placed in a culture vessel to which the cells do not adhere. Examples of non-adherent substrates include, but are not limited to, polystyrene and glass. The substrate may be untreated, or may be treated such that a negative charge is imparted to the cell culture surface. In addition, the cells may be plated in methylcellulose in culture media, or in normal culture media in hanging drops (Rudnicki, et al., 1987). Media which contains methylcellulose is viscous, and the embryonic stem cells cannot adhere to the dish. Instead, the cells remain isolated, and proliferate, and form aggregates.

In order to form aggregates in hanging drops of media, cells suspended in media are spotted onto the underside of a lid of a culture dish, and the lid then is placed on the culture vessel. The cells, due to gravity, collect on the undersurface of the drop and form aggregates.

In accordance with another aspect of the present invention, there is provided an embryonic stem cell. The embryonic stem cell has been engineered with DNA which encodes a protein or polypeptide which promotes differentiation of the cell into a specific cell line.

The DNA which encodes a protein or polypeptide which promotes differentiation of the embryonic stem cell into a specific cell line is DNA encoding a protein or polypeptide which is normally found in the specific differentiated cell line. Preferably, the protein or polypeptide which is present in the specific cell line is a protein or polypeptide which generally is not present in other types of cells.

In one embodiment, the DNA which encodes a protein or polypeptide which promotes differentiation of the embryonic stem cell into a specific differentiated cell line is DNA encoding a transcription factor present in the specific cell line to promote differentiation of the cell into the specific cell line.

In one embodiment, the DNA encoding a transcription factor is DNA encoding a transcription factor present in neuronal cells, and the specific cell line is a neuronal cell line.

In another embodiment, the DNA encoding a transcription factor is DNA encoding a transcription factor, such as the MyoD gene, present in muscle cells, and the specific cell line is a muscle cell line.

In yet another embodiment, the DNA encoding a transcription factor is DNA encoding a transcription factor present in hematopoietic cells, and the specific cell line is a hematopoietic cell line.

The DNA which encodes a protein or polypeptide which promotes differentiation of the embryonic cell into a specific cell line may be isolated in accordance with standard genetic engineering techniques (such as, for example, by isolating such DNA from a cDNA library of the specific cell line) and placed into an appropriate expression vector, which then is transfected into embryonic stem cells.

Appropriate expression vectors are those which may be employed for transfecting DNA into eukaryotic cells. Such vectors include, but are not limited to, prokaryotic vectors such as, for example, bacterial vectors; eukaryotic vectors, such as, for example, yeast vectors and fungal vectors; and viral vectors, such as, but not limited to, adenoviral vectors, adeno-associated viral vectors, and retroviral vectors. Examples of retroviral vectors which may be employed include, but are not limited to, those derived from Moloney Murine Leukemia Virus, Moloney Murine Sarcoma Virus, and Rous Sarcoma Virus.

In a preferred embodiment, cDNA is synthesized from RNA isolated by the method of Chomczynski, et al., *Anal. Biochem.*, Vol. 162, pgs. 156–159 (1987) from cells of interest. All RNA preparations are screened for the presence of large RNAs with gene probes that recognize high molecular weight mRNA (i.e., greater than 6 kb) on Northern blots. For example, all RNA preparations from neural cells may be screened for detection of MAP2 mRNA on Northern blots. (MAP2is a brain specific protein present in low abundance and coded for by a messenger RNA of about 9 kb. The ability to detect MAP2 messenger RNA on a Northern blot is a stringent test for the presence of intact high quality RNA.)

For cDNA synthesis, a single tube method developed by Gubler, *Nucl. Acids Res.*, Vol. 16, pg. 2726 (1988) is employed, and conditions are optimized to yield the greatest amount of full length cDNA product (about 7.5 kb in length). The cDNA is inserted into the pcDNA3 vector (Invitrogen), which allows for expression of the cDNA insert in mammalian cells. The pcDNA3 vector contains the cytomegalovirus (CMV) promoter, the SV40 origin of replication, the neomycin resistance gene for selection in eukaryotic cells, and the ampicillin resistance gene for selection in bacteria such as *E.coli*.

cDNA libraries are constructed wherein all the clones are oriented in the proper orientation for expression. Such is achieved by synthesizing oligo (dT) primed libraries with an oligo (dT) primer that includes a NotI site, and after cDNA synthesis, a BstXI adapter is ligated to the cDNA. Finally, the cDNA is digested with NotI (an enzyme that cuts infrequently in eukaryotic genes), thus creating a cDNA with a NotI overhang at the 3' end and a BstXI overhang at the 5' end. The cDNA then is ligated into pcDNA3 digested with BstXI and NotI. This places the 5' end of the cDNA downstream from the CMV promoter.

To enrich for developmentally expressed genes, libraries from uninduced embryonic stem cells are screened with labeled cDNA from differentiated embryonic stem cells and all cross-hybridizing clones are eliminated from further analysis. Such method allows the removal of those elements common to differentiated and undifferentiated cells. Also, subtractive cDNA libraries are constructed according to the method of Sive, et als., *Nucl. Acids Res.*, Vol. 16, pg. 10937 (1988). Subtractive cDNA libraries are cDNA libraries that are enriched for genes expressed in one cell type but not in another. The method relies on removal of common DNA sequences through hybridization of similar DNA sequences, and then the removal of these hybridized double-stranded DNAs. A subtractive cDNA library that contains sequences specific for a particular cell type derived from induced embryonic stem cells is generated. Single stranded cDNA is synthesized from uninduced cells. To select for those genes that are specific for the desired cell line derived from embryonic stem cells, genes that are expressed both in the induced cells and the non-induced embryonic stem cells are removed. Thus, RNA which is isolated and purified from embryonic stem cells that have differentiated into a desired cell line is hybridized to an excess of cDNA synthesized from uninduced embryonic stem cells to insure that all common elements are removed. RNA and cDNA common to both the induced and uninduced embryonic stem cells will hybridize, and these hybrids are removed. To remove double-stranded material, cDNA from uninduced embryonic stem cells is covalently modified with photoactivatable biotin (Sive, et al., 1988), and the hybrid can be removed by a simple phenol extraction because the biotin on the cDNA will cause the hybrid to partition to the phenol phase while the non-hybridized RNA will partition to the aqueous phase. Following this selection, RNA species found specifically in differentiated embryonic stem cells are used to construct cDNA libraries as hereinabove described.

Plasmid DNA containing cDNA inserts then are electroporated into embryonic stem cells. Cells are transfected with a plasmid that contains sequences for neomycin resistance and stable transfectants are isolated based on neomycin resistance. Stable transfected clones are isolated and induced with an appropriate agent, or with leukemia inhibitory factor (LIF) withdrawal alone, and scored for an increased ability to differentiate in response to these induction signals. Clones also are examined to determine if they are differentiating spontaneously in the presence of LIF.

In accordance with another aspect of the present invention, there is provided a method of producing a desired cell line from embryonic stem cells. The method comprises engineering embryonic stem cells with DNA which encodes a protein or polypeptide which promotes differentiation of the embryonic stem cells into a specific cell line. The embryonic stem cells then are stimulated with an agent which promotes differentiation of the embryonic stem cells into the desired cell line.

In one embodiment, the DNA which encodes a protein or polypeptide which promotes differentiation of the embryonic stem cells into a specific cell line is DNA encoding a transcription factor present in neuronal cells and said agent is selected from the group consisting of retinoic acid and nerve growth factor. In one alternative, the cells also may be grown in the presence of a cytokine such as those hereinabove described.

In another embodiment, the DNA which encodes a protein or polypeptide which promotes differentiation of the embryonic stem cells into a specific cell line is DNA encoding a transcription factor, such as, for example, the MyoD gene, present in muscle cells and said agent is a bipolar agent such as dimethylsulfoxide or hexamethylene bis-acrylamide. In one alternative, the embryonic stem cells also may be grown in the presence of a cytokine.

The embryonic stem cells may be engineered with the DNA and cultured under conditions hereinabove described. For example, prior to induction, the embryonic stem cells are engineered with DNA which encodes a protein or polypeptide which promotes differentiation of the embryonic stem cells into a specific cell line. Then, the embryonic stem cells may be cultured under conditions which provide for a three-dimensional network of such cells.

Also, it is to be understood that, within the scope of the present invention, that the embryonic stem cells may be used for gene therapy purposes. The embryonic stem cells may be engineered with DNA encoding a desired therapeutic agent. Such engineering may be accomplished by using expression vectors such as those hereinabove described. Once the cells are engineered with DNA encoding a desired therapeutic agent, the cells then are engineered with DNA which encodes a protein or polypeptide which promotes differentiation of the embryonic stem cells into a specific desired cell line, and/or stimulated with an agent which promotes differentiation of the embryonic stem cells into a desired cell line. The differentiated cells then may be administered to a host, such as a human or non-human host, as part of a gene therapy procedure.

In addition, there is also provided within the scope of the present invention, a method of screening embryonic stem cells for proteins which induce differentiation of embryonic stem cells into desired cell lines. In such method, RNA is obtained from specifically desired cells or tissues (such as for example, brain cells), and cDNA libraries are then constructed and placed into expression vectors. The libraries may be normal cDNA libraries or they may be subtractive cDNA libraries, i.e., such DNA libraries include DNA found in the desired cells or tissues but not in other cells or tissues. The expression vectors are then transfected into eukaryotic cells, such as COS cells. The cell culture supernatant then may be applied to embryonic stem cell cultures to determine if any secreted proteins from such cells induce differentiation of embryonic stem cells to a specific cell type. The cDNA from cells which induce differentiation of embryonic stem cells to a specific cell type then is evaluated further in order to determine which individual clones of such cDNA libraries induce differentiation of embryonic stem cells to a specific cell type. Once a specific cDNA which induces differentiation of embryonic stem cells to a desired cell type is identified, such cDNA then may be isolated and cloned into an appropriate expression vector, which may be transfected into undifferentiated embryonic stem cells or the expressed, purified protein may be added directly to cultured embryonic stem cells.

In one embodiment, such screening may be carried out by pooling bacterial clones, from the cDNA library prepared as hereinabove described, into groups of 1,000, and isolating plasmid DNA from the pooled clones. The plasmid DNA's then are electroporated into COS cells, such as COS-7 cells, for expression. After allowing from 48 to 72 hours for expression of transfected genes, tissue culture supernatant from transfected COS cells is harvested and applied to embryonic stem cells to determine if any secreted proteins from the COS cells can induce differentiation of embryonic stem cells. Supernatants from mock transfected cells (cells transfected with the plasmid alone) are tested in parallel to control for any non-specific effects of COS cell derived proteins. Embryonic stem cell differentiation may be screened by several means: (i) by microscopic observation of overt changes in embryonic stem cell morphology; (ii) by measuring changes in neuron specific gene expression on Northern blots with probes to neuron specific markers such as neuron specific enolase, GAP-43, and MAP2; and (iii) by loss of expression of a carbohydrate surface marker present only on undifferentiated stem cells recognized by the monoclonal antibody SSEA-1 (Ozawa, et al., Cell. Diff., Vol. 16, pp. 169–173 (1985)).

When a pool has been identified that expresses inducing capacity, that pool of cDNA clones is broken down further into smaller pools of 100 clones, and these sub-pools are transfected into COS cells. Supernatants are screened for inducing activity. Once appropriate sub-pools are identified, the clones are plated in 96 well dishes, and rows and columns are combined. The pooled columns and rows then are transfected into COS cells, and supernatants again are screened for activity. By analyzing the columns and rows that exhibit activity, the exact clone expressing inducing activity can be identified. This clone then is tested for ability to induce differentiation. After initial identification of potential factors, full-length cDNA clones are isolated and sequenced. Sequenced clones then are compared to other cloned genes in the DNA data base for homology or identity with previously cloned genes. Once a novel gene is identified, the gene is cloned into a stable expression system, the protein is purified, and its biological activity is tested. Sequencing of DNA is performed by standard protocols. Biologically active protein is prepared by standard chromatographic methods.

Alternatively, cDNA from differentiating embryonic stem cells or from embryonic organs and brain regions can be introduced directly into embryonic stem cells, and embryonic stem cell supernatants are screened for inducing activity.

The differentiated stem cells may be employed by means known to those skilled in the art to treat a variety of diseases or injuries. For example, stem cells which have differentiated into neuronal cells may be administered to a patient, such as, for example, by transplanting such cells into a patient, to treat diseases such as Huntington's disease, Parkinson's disease, and Alzheimer's disease. Such neuronal cells also may be employed to treat spinal cord injuries or chronic pain. Also, stem cells which have differentiated into muscle cells may be employed in treating muscular dystrophy, cardiomyopathy, congestive heart failure, and myocardial infarction, for example.

The invention will now be described with respect to the following examples; however, the scope of the present invention is not intended to be limited thereby.

EXAMPLE 1

Undifferentiated embryonic stem cells (ES-E14TG2a, purchased from the American Type Culture Collection, catalog no. ATCC CRL 1821) are maintained in Dulbecco's modified Minimal Essential Medium (DMEM) supplemented with glutamine, β-mercaptoethanol, 10% (by volume) horse serum, and human recombinant Leukemia Inhibitory Factor (LIF). The LIF replaces the need for maintaining embryonic stem cells on feeder layers of cells, and is essential for maintaining embryonic stem cells in an undifferentiated state.

In order to promote the differentiation of the embryonic stem cells into neuronal cells, the embryonic stem cells are trypsinized and washed free of LIF, and placed in DMEM supplemented with 10% (by volume) fetal bovine serum (FBS). After resuspension in DMEM and 10% FBS, $1\times10^6$ cells are plated in 5 ml DMEM plus 10% FBS plus 0.5 $\mu$M retinoic acid in a 60 mm Fisher brand bacteriological grade Petri dish. In such Petri dishes, embryonic stem cells cannot adhere to the dish, and instead adhere to each other, thus forming small aggregates of cells. Aggregation of cells aids in enabling proper cell differentiation. After two days, aggregates of cells are collected and resuspended in fresh DMEM plus 10% FBS plus 0.5 $\mu$M retinoic acid, and replated in Petri dishes for an additional two days. Aggregates, now induced four days with retinoic acid, are trypsinized to form a single-cell suspension, and plated in medium on poly-D-lysine-coated coated tissue culture grade dishes. The stem cell medium is formulated with Kaighn's modified Ham's F12 as the basal medium with the following supplements added:

15 $\mu$g/ml ascorbic acid
0.25% (by volume) calf serum
6.25 $\mu$g/ml insulin
6.25 $\mu$g/ml transferrin
6.25 $\mu$g/ml selenous acid
5.35 $\mu$g/ml linoleic acid
30 pg/ml thyroxine (T3)
3.7 ng/ml hydrocortisone
1. ng/ml Heparin 10 ng/ml somatostatin
10 ng/ml Gly-His-Lys (liver cell growth factor)
0.1 $\mu$g/ml epidermal growth factor (EGF)
50 $\mu$g/ml bovine pituitary extract (BPE)

Such medium provides for consistent differentiation of the stem cells into neuronal cells, and provides for survival of the neuronal cells for a period of time greater than 3 days, and selectively removes dividing non-neuronal cells from the population. The poly-D-lysine promotes the attachment of the neuronal cells to the tissue culture plastic, and prevents detachment of the cells from the dish and the formation of floating aggregates of cells. The cells are cultured for 5 days. Upon culturing the cells in the above medium, a culture of cells in which greater than 90% of the cells are neuronal cells is obtained. Such neuronal cells, which express the neurotransmitter gamma amino butyric acid (GABA), then may be employed for the treatment of the neural degeneration disease Huntington's disease. Through genetic engineering, these cells can be directed to express dopamine (for the treatment of Parkinson's disease) or acetylcholine (for the treatment of Alzheimer's disease).

EXAMPLE 2

Undifferentiated embryonic stem cells (ES-D3, purchased from the American Type Culture Collection as ATCC catalog no. ATCC CRL 1934) are maintained in supplemented Dulbecco's modified Minimal Essential Medium as described in Example 1. The embryonic stem cells then are trypsinized and washed free of LIF and placed in 1% (by volume) dimethylsulfoxide in DMEM plus 10% horse serum. Two days after the addition of dimethylsulfoxide and plating of cells in Petri dishes to form aggregates, the aggregates are collected and resuspended in fresh medium plus 1% dimethylsulfoxide. The aggregates are then plated onto multi-well untreated culture grade dishes without trypsin treatment. One aggregate is plated per well. The aggregates are cultured for 5 days. Upon culturing of the cells in multi-well dishes, cell cultures in which greater than 80% of the aggregates contain contracting muscle cells are obtained. Such cells may be used to treat cardiomyopathies, myocardial infarction, congestive heart failure, or muscular dystrophy.

EXAMPLE 3

Transfection of Embryonic Stem Cells with Mouse MyoD cDNA

For transfection of embryonic stem cells with mouse MyoD cDNA, both the D3 (ATCC catalog no. CRL 1934)

and E14 TG2a (ATCC catalog no. CRL 1821) embryonic stem cell lines were used. Embryonic stem cells were cultured as described in Robertson, 1987, except that the cells were maintained in media containing 5 ng/ml human recombinant leukemia inhibitory factor instead of on feeder layers.

Embryonic stem cells were co-transfected with pKJ1-Neo (Dinsmore, et al., *Cell*, Vol. 64, pgs. 817–826 (1991)), which carries the neomycin resistance gene for selection of stable transfectants, and with pEMCII (Davis, et al., *Cell*, Vol. 51, pgs. 987–1000 (1987)), which contains a portion of the mouse MyoD cDNA. pKJ1-Neo was linearized at the unique NsiI site and pEMCII was linearized at the unique ScaI site. In order to introduce the linearized plasmids into the embryonic stem cells, the embryonic stem cells were electroporated using a Gene Pulser (Bio Rad) in 0.4 cm gap distance electroporation cuvettes with the Gene Pulser set at 240 volts, 500μ Farads. For electroporation, $8\times10^6$ embryonic stem cells were suspended in 1 ml of HEPES-buffered saline (25 mM HEPES, 134 mM Na Cl, 5 mM KC1, 0.7 mM $Na_2 HPO_4$, pH 7.1) with 2 μg of linearized pKJ1-Neo and 20 μg PEMCII. After electroporation, the cells were plated at $5–7\times10^5$ per 35 mm gelatin coated culture dish in growth medium containing recombinant human leukemia inhibitory factor. The cells were allowed to grow for 36 hours and then Geneticin (Gibco-BRL), a commercial brand of neomycin, was added to the medium at a concentration of 400 μg/ml. The media containing the Geneticin was changed daily until clones of neomycin resistant cells could be identified (7 days after Geneticin addition). Individual neomycin resistant clones were isolated using glass cloning cylinders (Bellco).

Stable transfectants were isolated, expanded, frozen, and then stored in liquid nitrogen. 35 independent stably transfected embryonic stem cell lines were isolated. Ten of these cell lines have been analyzed, and have been found to express different amounts of MyoD as detected by Northern blots. Embryonic stem cell lines that were found to express high levels of MyoD RNA were found to have embryonic stem cells in the population that spontaneously differentiated into muscle cells as assessed by the staining of cells with a muscle specific myosin antibody. Those cell lines which showed high levels of MyoD expression were characterized further by inducing differentiation with dimethylsulfoxide. Cell lines which expressed high amounts of MyoD differentiated almost exclusively into skeletal muscle after dimethylsulfoxide induction. The percentage of cells that differentiated into skeletal muscle was greater than 90% as assessed by staining for muscle specific myosin, and by the ability of these cells to fuse and form myotubes that spontaneously twitch. In contrast, MyoD transformants that expressed very low amounts of MyoD differentiated into a mix of cardiac, smooth, and skeletal muscle indistinguishable from that derived from non-transfected embryonic stem cells. Additionally, there was no detectable difference between the D3 and E14 embryonic stem cell lines for MyoD expression or differentiation.

It is to be understood, however, that the scope of the present invention is not to be limited to the specific embodiments described above. The invention may be practiced other than as particularly described and still be within the scope of the accompanying claims.

What is claimed is:

1. A process for producing neuronal or muscle cells selectively from embryonic stem cells, comprising:

culturing embryonic stem cells in a differentiation culture medium and in the presence of an agent which promotes differentiation of said embryonic stem cells into desired cells selected from the group consisting of neuronal and muscle cells, said embryonic stem cells having been grown previously in a growth culture medium which differs from the differentiation culture medium, said differentiation culture medium promotng growth of the embryonic stem cells at a growth rate which is from about 10% to about 80% of the growth rate of embryonic stem cells in said growth culture medium, wherein when the desired cells are neuronal cells, said agent is selected from the group consisting of retinoic acid, nerve growth factor; and wherein when the desired cells are muscle cells, the agent is selected from the group consisting of dimethylsulfoxide and hexamethylene bis-acrylamide.

2. The process of claim 1 wherein said differentiation culture medium contains fetal bovine serum at a concentration of about 10% by volume.

3. The process of claim 1 wherein said agent is retinoic acid.

4. The process of claim 3 wherein, in addition to culturing said embryonic stem cells in the presence of said retinoic acid, said embryonic stem cells are grown in the presence of a cytokine.

5. The process of claim 1 wherein said agent is dimethylsulfoxide.

6. The process of claim 1 wherein said agent is hexamethylene bis-acrylamide.

7. The process of claim 1 wherein, in addition to culturing said embryonic stem cells in the presence of an agent selected from the group consisting of dimethylsulfoxide and hexamethylene bis-acrylamide, said embryonic stem cells are grown in the presence of a cytokine.

* * * * *